(12) United States Patent
Greter et al.

(10) Patent No.: US 8,282,596 B2
(45) Date of Patent: Oct. 9, 2012

(54) BREASTPUMP WITH LETDOWN FEATURE

(75) Inventors: Andy Greter, Steinhausen (CH);
Richard S. Weston, Carlsbad, CA (US);
Brian H. Silver, Cary, IL (US); Michael Larsson, Zug (CH)

(73) Assignee: Medela Holding AG, Baar (CH)

( * ) Notice: Subject to any disclaimer, the term of this patent is extended or adjusted under 35 U.S.C. 154(b) by 1541 days.

(21) Appl. No.: 10/413,463

(22) Filed: Apr. 14, 2003

(65) Prior Publication Data

US 2004/0024351 A1 Feb. 5, 2004

Related U.S. Application Data

(63) Continuation-in-part of application No. 09/475,681, filed on Dec. 30, 1999, now Pat. No. 6,547,756, and a continuation-in-part of application No. 10/114,686, filed on Apr. 2, 2002, now Pat. No. 6,808,517, which is a continuation-in-part of application No. 09/476,076, filed on Dec. 30, 1999, now abandoned.

(60) Provisional application No. 60/170,070, filed on Dec. 10, 1999.

(51) Int. Cl.
*A61M 1/06* (2006.01)

(52) U.S. Cl. .......................................... 604/74; 604/76

(58) Field of Classification Search .................... 604/73, 604/74–76, 313, 314, 315, 346, 350, 500, 604/514; 119/14.02
See application file for complete search history.

(56) References Cited

U.S. PATENT DOCUMENTS

| 4,772,262 | A | * | 9/1988 | Grant et al. | 604/74 |
| 5,571,084 | A | * | 11/1996 | Palmer | 604/74 |
| 5,843,029 | A | * | 12/1998 | Bachman et al. | 604/74 |
| 5,902,267 | A | * | 5/1999 | Medo | 604/74 |
| 6,045,529 | A | * | 4/2000 | Nuesch | 604/74 |
| 6,273,868 | B1 | * | 8/2001 | Nordvik | 604/74 |
| 6,673,036 | B1 | * | 1/2004 | Britto | 604/74 |
| 7,101,350 | B2 | * | 9/2006 | Ytteborg | 604/74 |
| 7,223,255 | B2 | * | 5/2007 | Myers et al. | 604/74 |

FOREIGN PATENT DOCUMENTS

| WO | WO 99/44650 | * | 9/1999 |
| WO | WO 99/44650 | * | 10/1999 |

* cited by examiner

*Primary Examiner* — Kevin C Sirmons
*Assistant Examiner* — Andrew Gilbert
(74) *Attorney, Agent, or Firm* — McDonnell Boehnen Hulbert & Berghoff LLP (57) ABSTRACT

Breastpumps and methods for use in extracting breastmilk, which can be used to generate, among other things, both a letdown or stimulation phase and a milk expression phase, are disclosed.

12 Claims, 9 Drawing Sheets

STANDARD CLASSIC PROGRAM

SUCTION CURVES AND CYCLES EQUAL TO CLASSIC
VACUUM RANGE: 100-250 mmHg
CYCLES: 47/min (NOT ADJUSTABLE)

FIG. 6

SORE NIPPLE PROGRAM

EXTREMELY GENTLE AND SLOW SUCTION
DECREASED VACUUM YIELDS GENTLER AND SLOWER SUCTION
VACUUM RANGE: 20-250
CYCLES: 25-40/min (CONTROLLED BY VACUUM LEVEL)

BREASTPUMP WITH LETDOWN FEATURE

This application is a continuation-in-part of Ser. No. 09/475,681, filed Dec. 30, 1999, now U.S. Pat. No. 6,547,756, and U.S. patent application Ser. No. 10/114,686, filed Apr. 2, 2002 now U.S. Pat. No. 6,808,517, which is a continuation-in-part of U.S. patent application Ser. No. 09/476,076, filed Dec. 30, 1999 now abandoned, all of which claim the benefit of U.S. Provisional Application No. 60/170,070, filed Dec. 10, 1999.

FIELD OF THE INVENTION

This invention relates to breastpumps for drawing breastmilk, and particularly to a breastpump whether operated manually or motorized, so as to produce both a stimulation, or a letdown phase, and an expression phase.

BACKGROUND OF THE INVENTION

Breastpumps for use by nursing mothers are well known. They allow the nursing woman to express the breastmilk as necessary or convenient, and further provide collection of the breastmilk for later use. For some mothers, breastpumps may be a necessity, such as when the child has suckling problems, or if the mother has problems with excessive or deficient milk production, or soreness, deformation or injury of the mammilla, or like conditions which are not conducive to manual breast feeding.

Manual breastpumps are commonplace. They are relatively inexpensive and easy to transport. Examples of such manually-driven pumps are in U.S. Pat. No. 6,497,677.

Electrically-driven breastpumps are also commonplace. They may be of a substantially large size of a non-portable or semi-portable type, typically including a vacuum pump which has an electric motor that plugs into standard house current. Besides eliminating the efforts of manual pumping, some advantages of this type of pump include better controllability and regulation of the vacuum. The option of variable frequencies (rates) and amplitudes (suction levels) is often provided.

Battery-driven breastpumps have also been developed. These breastpumps have the advantages of controllability and regulation of the vacuum, as well as being easily carried. Such a battery-driven portable breastpump is described in U.S. Pat. No. 4,964,851, for example. This breastpump, sold under the name MINIELECTRIC by Medela, Inc., is lightweight and achieves good vacuum (i.e., negative pressure) regulation in preferred limits, for example, between about 100 and about 220 mmHg. The LACTINA breastpump sold by Medela, Inc. is also another type of breast pump which may be driven by battery as well as house current. It is generally disclosed in U.S. Pat. No. 5,007,899.

The prior art manual as well as motorized breastpumps have, to Applicants' knowledge, only been developed with a single type of "cycle" for a given pump. That is, the driving mechanism for generating the vacuum (negative pressure) to be applied at the breast in the more sophisticated pumps is geared to a particular sequence, or curve, of negative pressure increase (i.e., increasing suction), and then release. In these pumps, regardless of vacuum amplitude and frequency, the envelope of the curve (vacuum over time) is essentially the same, barring unintended defects occurring at extreme settings. The curve is often aimed at reproducing in some sense the suckling action of an infant, for instance.

Breast pumping can cover a range of different conditions, however, such as where the mother's nipples are sore for some reason, there is a state of significant engorgement, some nipple stimulation may be particularly desired, letdown and relaxation may be of particular interest, it may be desired to increase milk production, and so on.

As noted above, some breastpumps provide the user with the ability to vary the amount of vacuum being applied, as well as the speed of the pumping action (i.e., number of vacuum cycles per minute). In some instances, speed and vacuum level may influence each other, such that as speed increases so does the vacuum level. The basic "curve" remains fixed, however, as described above, and the user must adapt as best she can to making variations within that particular curve built into the machine, which typically has been generalized for the overall population of users.

Moreover, conventional breastpumps are not made to differentiate between different phases of the milk expression process, or equipped with a mechanism or method of operation to accommodate the different phases. That process includes, for example, a period before breastfeeding, referred to as the milk ejection period, or "letdown", in which effective removal of the milk from the breast is initiated by the suckling action of a baby's mouth and jaw to produce or stimulate an ejection reflex, in which stored milk is released and made available for general expression. It is believed that efficient expression of breastmilk is improved by stimulating milk ejection before initiating milk expression.

"Letdown" is, of course, a well known phenomenon. The milk ejection reflex is the neurohormonal reflex resulting from the tactile stimulation of the nipple sending neuronal impulses to the hypothalamus, and the neurohypophysial release of oxytocin into the systemic circulation. The subsequent contraction of the myoepithelial cells within the breast caused by oxytocin moves milk from the alveoli into the collecting ducts and forward to the nipple. Milk ejection, or the milk ejection period, is the interval when an increased availability of milk from the nipple is caused as a result of the stimulation of the milk ejection reflex. Milk ejection in women normally lasts for approximately two minutes, but will, of course, vary from person to person. The ejection reflex will be identified in the following also as "letdown" or "ejection".

The level of pressure applied and the intermittency of the stimulation for initiating ejection are different than the level and intermittency of the action for actually expressing the breast milk. Conventional breastpumps do not provide a method or mechanism by which a user can easily stimulate an ejection reflex and subsequently commence to efficiently express breastmilk.

A demand is therefore believed present for a breastpump that is usable to easily produce stimulation to initiate ejection, and in addition provides efficient expression of breastmilk, thereafter by operation thereof.

SUMMARY OF THE INVENTION

It is a principal objective of the present invention to provide a breastpump including a mechanism that can be used to generate a letdown sequence. In one form, the breastpump further includes a plurality of differing milk expression (extraction) sequences or curves, or changing combinations of conditions over time, which effectively address different phases of breastmilk production. The invention in one form includes a breastpump comprising a breastshield having a portion within which a woman's breast is received for the expression of milk. One or more sources of pressure change (e.g., vacuum) communicate with the breastshield. The source(s) of pressure is operated so as to effectively elicit letdown and then a different phase of breastmilk production, such as general milk expression.

The source of vacuum, in one embodiment, is operated manually, i.e., by physically manipulating a pump mechanism of the manual breastpump with the hand. The source of vacuum is operated by a motor drive or the like in another embodiment, with the motor drive being adjustable according to selections made by the user. In still another embodiment, the source of vacuum is operated by a motor, according to a controller with preset instructions or user input instructions, and may automatically transition between different operating conditions according to the preset instructions or operate according to a user's input, or both.

It will be understood that in each of the embodiments, there is a mechanism for operating the source(s) of pressure change (e.g., vacuum) according to at least a first set of conditions and a second set of conditions. While a negative pressure is typical for breastpumps, a positive pressure is also usable in some adaptations. For purposes of the present invention, one of the set of conditions corresponds to a letdown condition. The second set of conditions is at least one sequence for pumping that is not for letdown, such as a general milk expression condition. A significant, and heretofore unavailable advantage realized by the present invention is also the ready ability to modify the breastpump suction action to a variety of desired generally expression conditions, and provide this ability to the end-user.

In yet another aspect of the invention, an improved motorized breastpump is provided which has a pre-programmed milk letdown sequence. The letdown sequence is most advantageously made available through a button, switch or the like provided on the breastpump used to initiate the sequence.

The present invention in another significant aspect has a manually generated letdown mechanism which is designed to be easily manipulated to produce the staccato-like action considered advantageous to the ejection reflex.

These and other features and advantages of the present invention will be further understood and appreciated when considered in relation to the following detailed description of embodiments of the invention, taken in conjunction with the drawings, in which:

BRIEF DESCRIPTION OF THE DRAWINGS

FIG. 9 is another representation of a letdown sequence;

DETAILED DESCRIPTION OF EMBODIMENTS OF THE INVENTION

Figure 1:
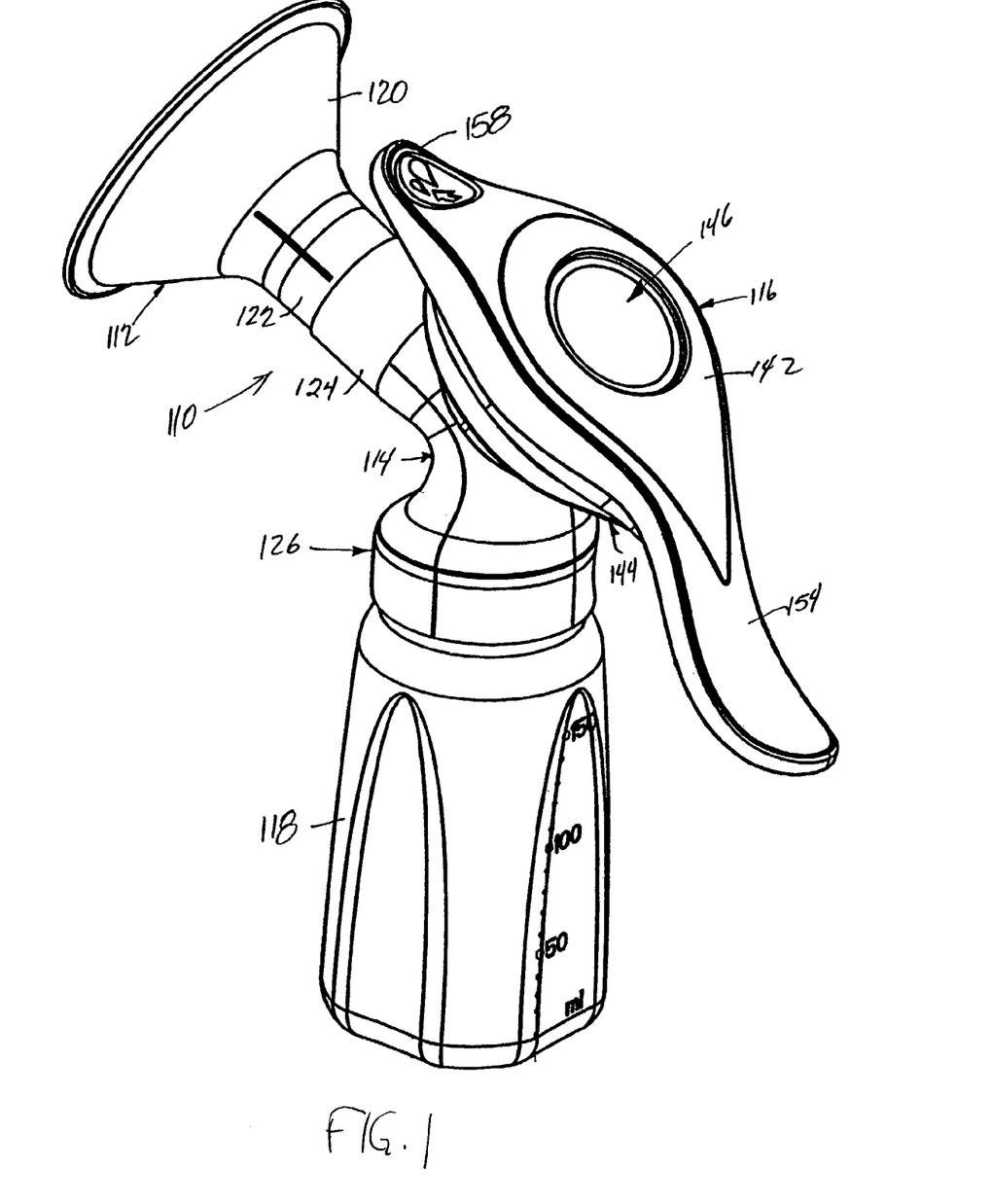
FIG. 1 is a perspective view of an embodiment of a manual breastpump according to certain aspects of the present invention.
Figure 2:
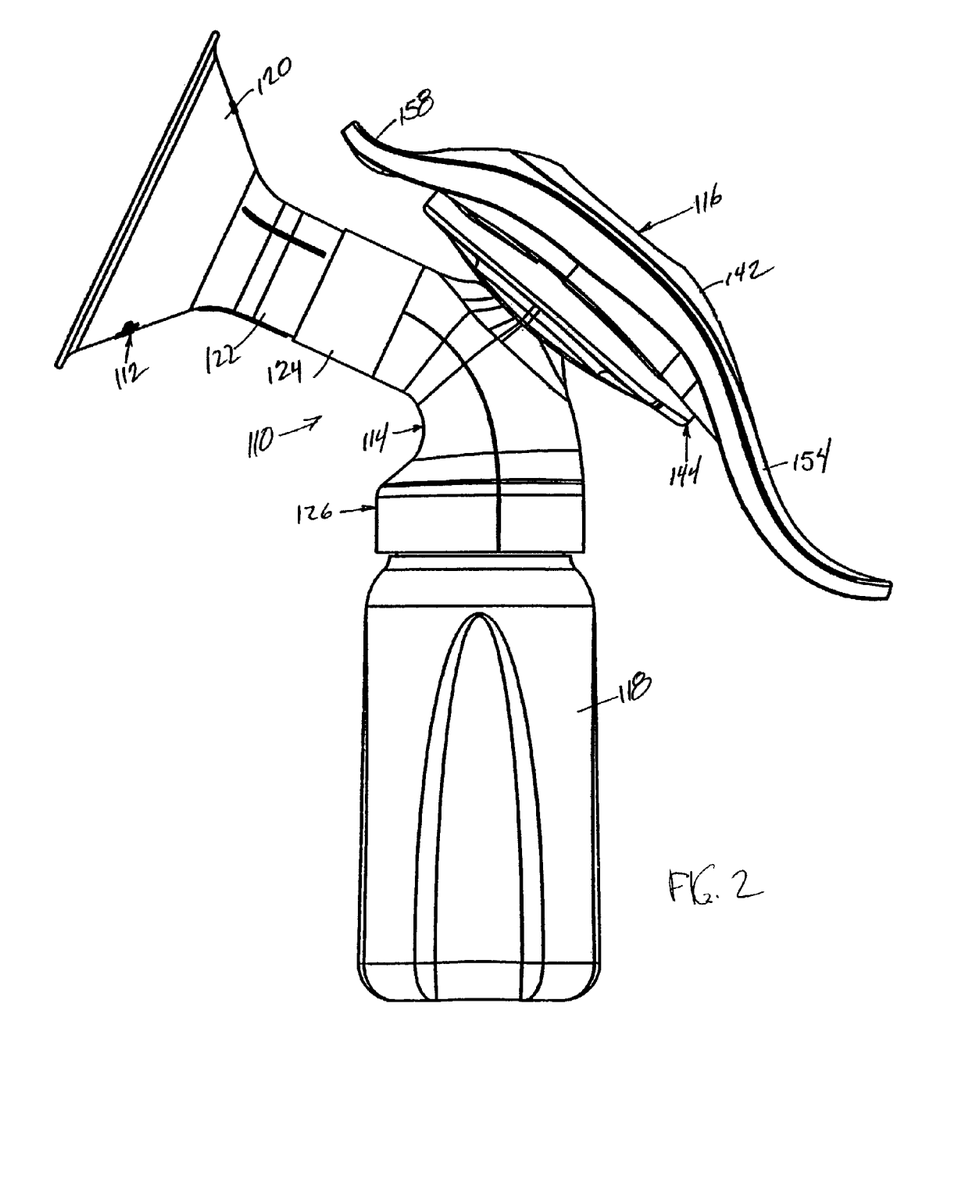
FIG. 2 is a side view of the breastpump of FIG. 1.
Figure 3:
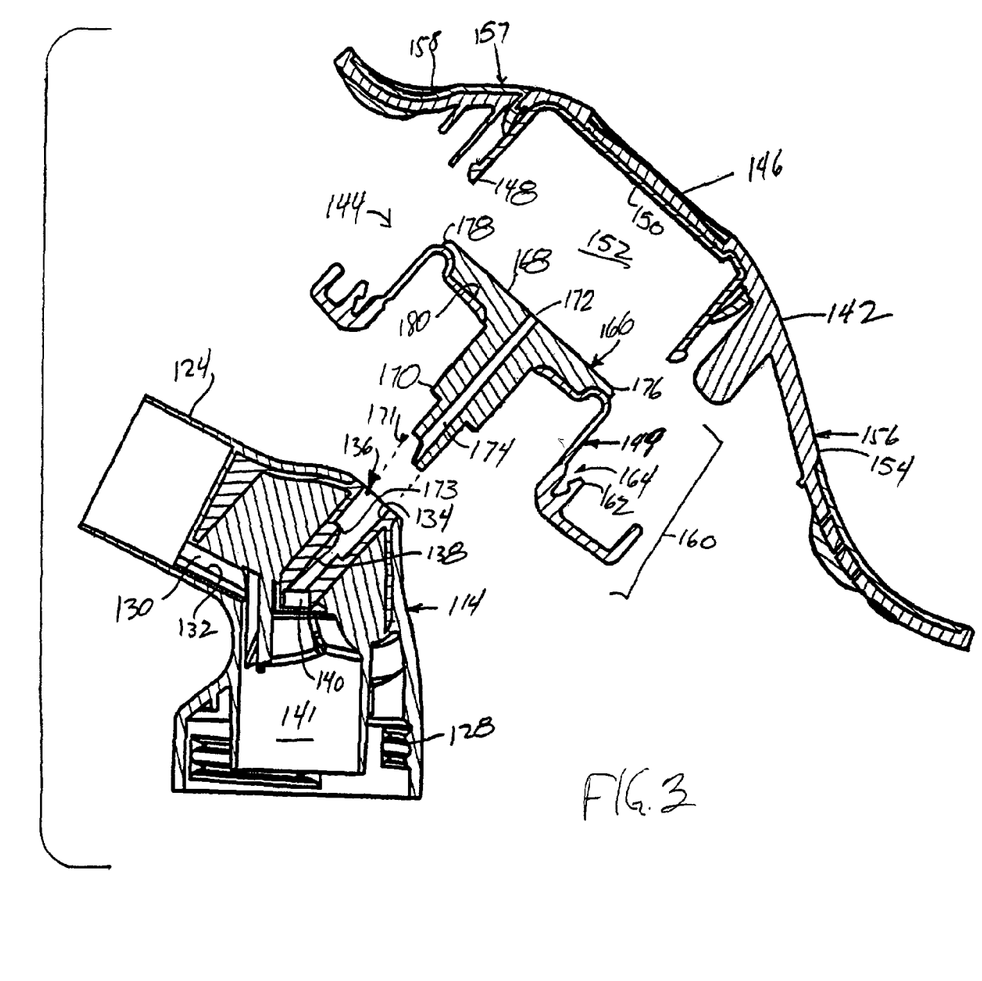
FIG. 3 is an exploded sectional view of the breastpump of FIG. 1.

One embodiment of the invention is a manual breastpump as detailed in U.S. Provisional Application No. 60/405,559 filed Aug. 23, 2002, incorporated herein by reference, and illustrated in FIGS. 1-3, depicted herein.

The breastpump assembly 110 includes a shield 112, for contacting the breast. The shield 112 is attached to a conduit structure 114. A vacuum pump mechanism 116 is attached to the conduit structure 114. The conduit structure 114 transmits vacuum generated in the vacuum pump mechanism 116 to the shield 112 and transmits expressed breastmilk from the shield to an attached container 118.

The shield 112 has a generally funnel shaped portion 120 shaped and sized for being received onto a breast. The shield 112 extends into a sleeve 122 downstream from the funnel shaped portion 120. The sleeve 122 is open so as to conduct expressed milk into the conduit structure 114. For purposes of the instant invention, the shape of the shield 112 and its formation with the conduit structure 114 are incidental; the particular arrangement and details of these elements is in no way limiting.

The conduit structure 114 is attachable to the shield 112 through a shield mount 124 sized and shaped to receive the sleeve 122. The conduit structure 114 is generally a housing that interconnects and permits fluid communication between parts of the breastpump assembly 110. The conduit structure 114 connects to the sleeve 122, by way of the shield mount 124 at the one end, and terminates with a valve mechanism as is known in the art at a container end 126. The container end 126 may include threads 128 or any suitable mechanism for releasable attachment to container 118, which may be in the form of a milk bottle or the like.

The conduit structure 114 includes a first conduit 130 defined by an inner first conduit surface 132 for conducting expressed breast milk from the shield mount 124 through the valve mechanism and into the container 118. The conduit structure 114 includes a receptacle 134 for receiving the pump mechanism 116. The receptacle 134 may be a bore formed in the conduit structure 114 or a bore formed in a cylindrical extension (not shown) of the conduit structure 114. The receptacle 134 further includes a longitudinal bore 138 in fluid communication with a second conduit 140 for transmitting pressure changes generated in the pump mechanism 116 through the receptacle 134 and conduit structure 114. The second conduit 140 is in fluid communication with the first conduit 130 in chamber 141 so as to conduct pressure changes through the conduit structure 114 to the shield 112 and thence to a breast of a user.

The pump mechanism 116 is releasably and even rotatably attachable to the conduit structure 114. The pump mechanism 116 includes two main portions. A first portion is a substantially rigid shell or handle 142. The second portion is a flexible movable member in the form of a diaphragm-like structure 144 attached to the handle. The handle 142 may be made of a rigid plastic similar to that of the conduit structure 114. Referring to FIG. 3 in particular, handle 142 has a central portion 146, which has the form of a dome or housing, and a bottom edge portion 148. The dome 146 includes an inner surface 150, which defines a vacuum chamber 152 with the diaphragm 144 as will be explained more fully below.

The handle 142 includes a first extension 154 in the form of a handle extending from a back side 156 of the handle 142, which is sized and shaped to be grasped by a hand or one or more digits of the user. Drawing the distal or first extension 154 toward the conduit structure 114 and generally toward the user's body operates the first extension 154 in one mode of operation of the breastpump. A second or proximal extension 158 extends from the front side 157, opposite the first extension 154, in the form of a tab or smaller handle extension. The proximal or second extension 158 may be smaller than the first 154 and may be operated by drawing the extension downwardly toward the conduit structure 114 in another mode of operation with a single digit of the user, as described hereafter. Distal and proximal are used herein relative to the shield 112.

The diaphragm 144 includes two main parts. A first part is a flexible portion 160, shaped like an inverted cup to be positioned inside the dome 146 of the handle 142 adjacent the inner surface 150 thereof. The flexible portion 160 includes an outer edge 162 with a channel 164 for tightly fitting with the dome shell edge 148. The flexible portion 160 is made of a naturally resilient material so that there is a tendency for the membrane to be resiliently returned to a starting position after being deflected in use. The membrane 160 includes a central concavity 180 on an upper surface thereof and a central opening to receive a puller 166. There is a thinned transition area 149 defining the middle of the flexible portion 160.

The second part of the diaphragm 144 is a rigid member or puller 166. The puller 166 includes a disc portion 168 and an extension or post 170. The disc portion 168 is a generally flattened oval member that is centrally imbedded within or attached to the membrane 160 at the upper surface concavity 180 and may be held in place by posts of the membrane 160 inserted through holes arranged somewhat symmetrically around the disc portion. The disc portion 168 includes a central opening 172 that is open to the vacuum chamber 152 at an upper end thereof. The post 170 is a hollow cylindrical member that is attached to the disc portion 168. A hollow bore 174 of the post 170 is aligned to be in communication with the central opening 172 of the disc portion 168. The extension 170 is sized and shaped to be received within the post receptacle 134, via a press or interference fit. Preferably, the connection of the extension 170 to the post receptacle 134 is releasable and rotatable or pivotable in the receptacle 134. In this manner, the entire handle 116 and extension 154 may be rotated to one side of the breastpump assembly for the convenience of the user. In an alternate embodiment, the puller 166 may be fixedly connected to the conduit structure 114. In yet another embodiment, the assembly 110 may be formed as a unitary unit. For ease of cleaning, it is preferred to provide the various elements of the assembly 110 as separate elements. Accordingly, for the purpose of this invention, the term connected may refer to a releasable or a permanent connection.

In one preferred embodiment, the lower end of the post 170 forms a half-lap feature 171, which when fitted to the receptacle 134 cooperates with a converse feature 173 within the bore of socket 134 to limit the arcuate travel of handle 116 and prevent over-rotation.

In operation, at a rest position, which is a start or initial position, the pump mechanism membrane 160 lies against or closely adjacent to the inner surface 150 of the dome portion 146 of the handle 142. In this position, as shown in FIG. 1, the volume of the vacuum chamber 152 is zero or at a minimum volume. When the user manipulates the first extension 154 by pulling the extension inwardly toward the conduit structure 114, the post 170 and disc portion 168 remain connected to and motionless with respect to the conduit structure while the handle 142 moves with the extension. The rigid disc portion 168 pivots about a point at a rear edge 176 thereof, causing the membrane 160 to pull away from the inner surface 150 of the dome 146, which expands the vacuum chamber 152 a first volume to produce a first negative pressure therein. The reduced pressure is communicated through the central opening 172 of the disc 168, through the hollow bore 174 of the post 170, through the longitudinal bore 138 of the receptacle 134, through the second conduit 140 and thence the shield 112. Operation of the breastpump 110 by this mode of operation is intended to generate an amount of vacuum at a cyclical rate in order to efficiently promote milk expression from a breast, i.e., general pumping. A very easily operated one-handed manual pump mechanism is thereby provided that operates a manual breastpump in a first mode of operation to produce an efficient expression of breast milk. Note also that the handle 142 freely rotates in receptacle 134, enabling the user to adjust the handle's position to a most convenient grasping orientation.

When the user manipulates the second extension 158 by pulling that extension downwardly (e.g., toward the conduit structure 114) in the other mode of operation, the membrane 160 pulls away from the inner surface 150 of the dome 146 at a distal region by pivoting about a point at a front edge 178 of the disc, which expands the vacuum chamber 152 a second volume to produce a second negative pressure therein.

The second volume may be less than the first volume so that a lesser relative change in pressure is generated by this mode of operation as compared to the one already described for general pumping. In the present embodiment, this difference may be due to the shape and travel of the first and second extensions 154, 158. That is, second extension travels a shorter distance before it is stopped by the hood mount 124. First extension 154 has a longer distance of travel before it is stopped by the conduit structure 114. In an alternate embodiment (not shown), the depth of the vacuum chamber adjacent the second extension 158 may be formed as to be greater than the depth of the chamber adjacent the first extension 154. When the pull of the puller 166 causes the membrane 160 to pull away from the inner surface 150 of the dome 146, a relatively greater change in volume is created in operation of the first extension 154 due to the greater depth of the resultant chamber as compared to manipulation of the second extension 158.

Operation of the breastpump 110 by manipulating the extension 158 in this mode of operation is intended to generate an amount of vacuum (relatively less in absolute change) at a cyclical rate (which may be relatively more rapid) in order to efficiently promote a milk ejection reflex, i.e., letdown. It can be seen that use of a small extension 158 is possible and efficient to promote ejection due to the lesser amount of vacuum generated in the second mode of operation. Because of the lesser amount of force necessary the second mode of operation may occur relatively more rapidly, which, it has been found, is desired to produce ejection as compared to expression.

Another embodiment of the invention is a motorized breastpump having the capability of producing vacuum and cycle frequency conditions corresponding to at least a letdown sequence and some other sequence, such as an expression sequence. The breastpump may be preprogrammed to do so, or may be user programmable as detailed in U.S. Pat. No. 6,547,756, incorporated herein by reference, or may have both capabilities. The breastpump may be operated according to the sequences and parameters detailed in U.S. patent application Ser. No. 10/114,686, incorporated herein by reference. For purposes of the present invention, the actual general expression sequence used is not limiting, since an inventive concept is the combination of a letdown feature with another sequence, such as generated by a general milk expression mechanism.

Figure 4:
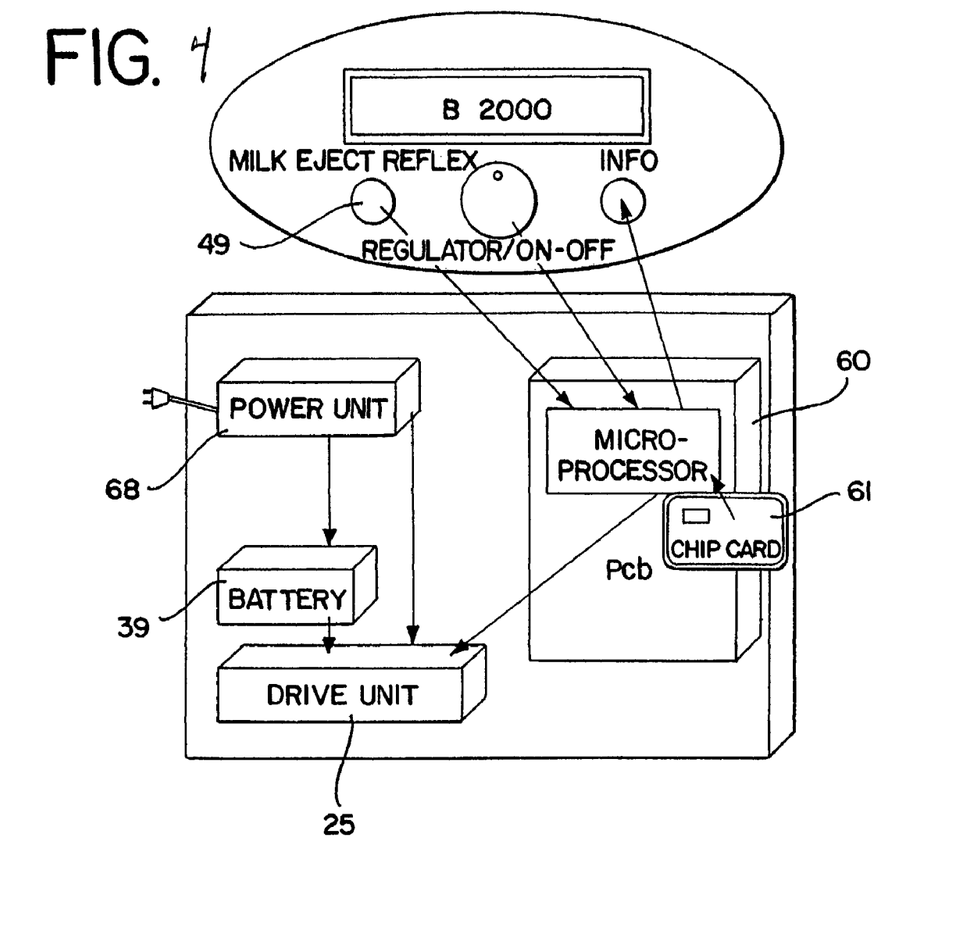
FIG. 4 is a diagrammatic representation of the interaction of various components within a programmable breastpump according to another embodiment of the present invention.

This motorized embodiment has the ability to program the breastpump with different types of suction sequences, or cycles as they are sometimes referred to herein. With reference to FIG. 4, for instance, the breastpump utilizes a microprocessor-based system indicated at 60 which is provided user input through a plurality of "chip" cards 61. Each chip card contains one or more predetermined programs recorded on an EEPROM. For example, each card could contain a specific type of sequence along with a milk letdown sequence.

An EEPROM microcontroller of the type MB90562 may be used, for one example, or the Atmel 2-wire EEPROM chipcard microcontroller AT24C164 for another. These provide about 16K of memory, which is considered presently sufficient.

The programs (some examples of which are described hereafter) are recorded in a conventional manner, and would be provided to the mother ready to use. The programmed chip card 61 engages an interface to the microprocessor. The particular program on the selected chip card 61 is then communicated to the microprocessor 60. Microprocessor 60 is integrated with the drive unit 25 to effect operation of the drive unit in accordance with the selected program, drawing upon either the AC power source as converted via standard technology to DC (indicated at 68 in FIG. 4), or from the battery source 39. The microprocessor 60 can also control power management.

One embodiment contemplated provides a milk letdown sequence (milk ejection reflex) that can be engaged without need of a chip card for the same. The milk letdown sequence (described below) is pre-programmed in the microprocessor 60, or may otherwise be wired into the circuitry in a manner to override the then-existing operating program. When the mother desires to engage this sequence, she presses the button 49, which produces and sends an electrical signal, as to the microprocessor 60. The letdown program is then caused to be effected.

It will be readily understood that a chip card 61 is but one way to program the microprocessor 60. Other input means could be used, such as more dedicated buttons like button 49, each set to actuate a given sequence pre-programmed into the microprocessor 60. A numeric pad could be provided to input a code. The programs could be provided through an electronic data link, such as a modem, or optically, or otherwise. Furthermore, the microprocessor may be provided with the capability to automatically transition from one sequence or cycle type to another and optionally to a third or more cycle types without input from the user.

It can thus be seen that a variety of different suction cycles or sequences can now be provided with the same breastpump equipment. An example of the kind of methods that such cycle could represent comprises FIGS. 5 through 9.

Figure 5:
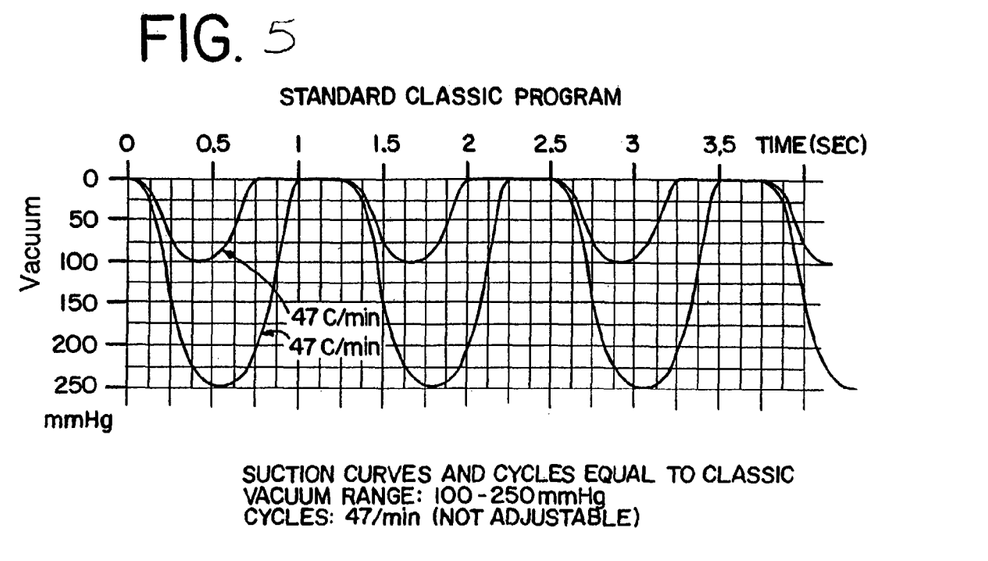
FIGS. 5 through 8 are various methods (curves) for operating a breastpump to differing ends, FIG. 7 being a curve for a letdown sequence.

FIG. 5, for instance, is what is referred to by Medela, Inc. as the "Standard Classic Program". This is a method for operating a breastpump that has been developed which is considered to provide a general optimal suction curve reminiscent of an infant's normal suckling, such as provided by the 015 "CLASSIC" breastpump sold by Medela, Inc. As indicated in the graph of FIG. 5, negative pressure is along the y-axis (in millimeters of mercury) and time (in seconds) along the x-axis. In this particular method, the cycles are fixed at about 47 per minute; the amount of suction is generally adjustable between about 100 to about 250 mmHg.

Figure 6:
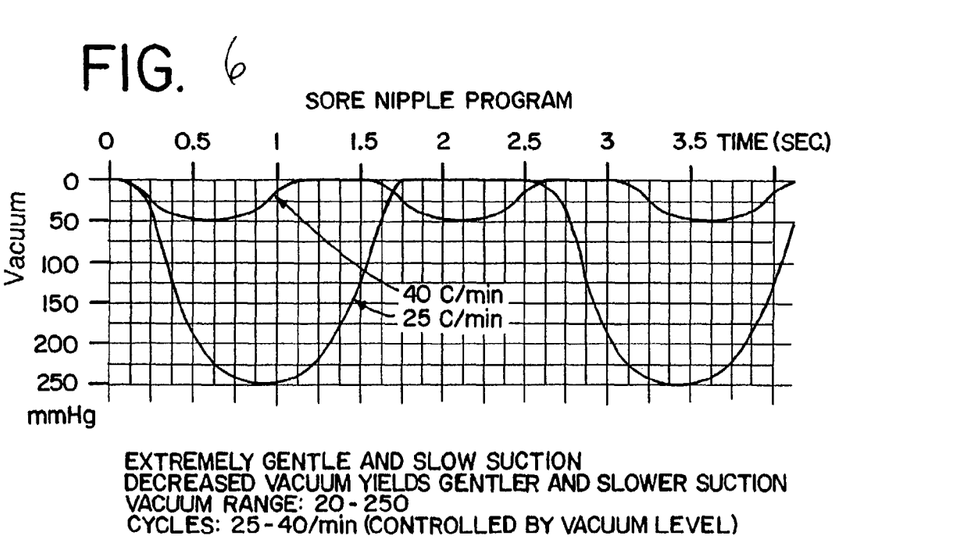

FIG. 6 illustrates what can be termed as a new "Sore Nipple Program" method. In comparison to FIG. 5, it will be seen that the lower end of the vacuum range is reduced to about 20 mmHg, and the overall suction cycle is extended in duration, i.e., from a low of about 25 cycles/min. to about 40. For a lower vacuum applied in this program, there is an increase in the number of cycles. In general, however, there is a slower and gentler suction compared with the "CLASSIC" program of FIG. 5.

Figure 7:
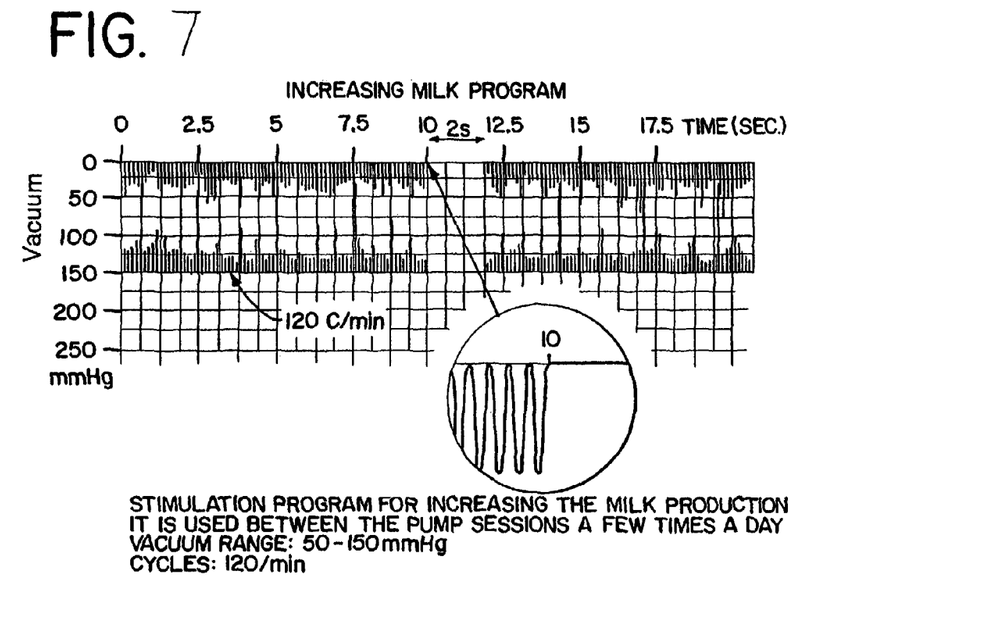

FIG. 7 shows a new method for operating a breastpump which is considered to yield an increase in milk output. This is a letdown sequence. This is also a program that might be applied between regular pump sessions several times a day. In this method, the breastpump is operated at a rapid cyclical rate on the order of about 120 cycles/min., preferably with a pause after a period of vacuum application; here, 10 seconds of vacuum, then a 2 second pause. The negative pressure is in the range of about 50 to about 150 mmHg. Note the detail in the inset of FIG. 7 showing the rapidity and steep slopes of the vacuum application.

Figure 8:
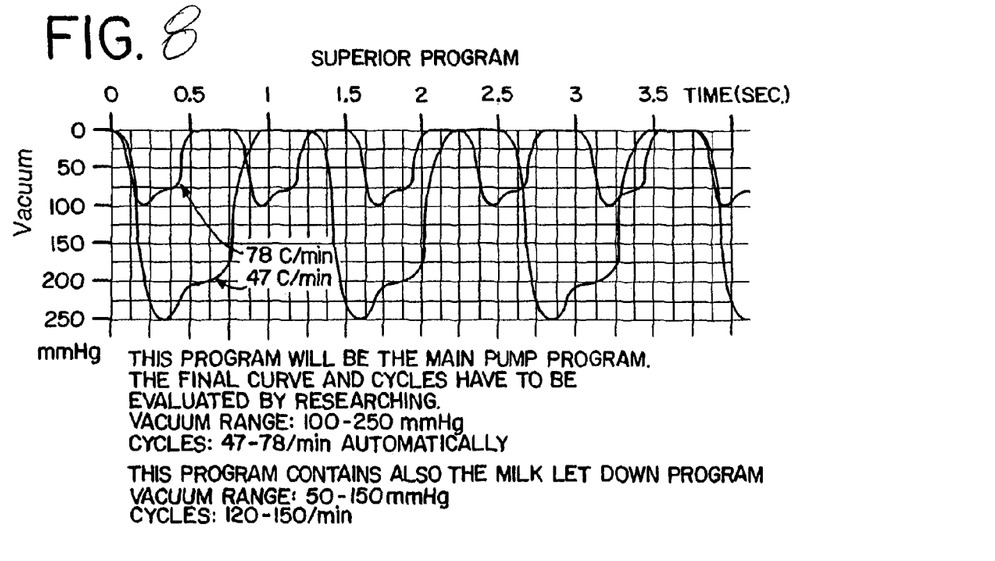

What has been termed a new "Superior Program" for operating a breastpump is illustrated in FIG. 8. A vacuum range of about 100 to about 250 mmHg has been chosen, with cycles ranging from about 47 to about 78 per minute. The cycle rate and the vacuum are tied, such that as, for instance, the cycles decrease, the amount of vacuum increases, i.e., there is an inverse relationship. It will be noted that this program differs from the "CLASSIC" program above in part through a sequence that initially reaches a peak negative pressure, then smoothly starts a pressure increase (less negative) along a similar (although opposite) slope to that of the negative pressure build-up, but then slows the pressure increase briefly, before continuing on essentially the initial slope for the negative pressure release. A milk letdown sequence is also incorporated in this "Superior Program," and utilizes a vacuum range of about 50 to about 150 mmHg, with cycles ranging between about 80 to about 160 per minute.

A preferred vacuum cycle for stimulating the milk ejection reflex by generating a rapid cyclical pressure change with a breastpump is shown in the graph of FIG. 9. The graph includes two separate curves, but with the same envelope or overall pattern. A first curve C, which ranges in pressure from 0 mmHg (atmospheric) to about −45 mmHg (vacuum), the minimum curve C, represents the lower limit of the range of the vacuum cycle (lower amount of peak vacuum). A second curve D, which ranges in pressure from 0 mmHg to about −225 mmHg, the maximum curve D, represents the high limit of the range of the vacuum cycle (highest amount of peak vacuum). The minimum and maximum curves C, D differ in amplitude and share an envelope.

It can also be seen from the graph of FIG. 9 that the time duration of each of the minimum and maximum cycles C, D does not vary with the amplitude of the vacuum. In other words, in a curve cycle where the peak amplitude of the vacuum is greater, the time duration of the entire cycle is the same as that of curve having a lesser peak amplitude. In the illustrated cycle, the time duration of the cycle remains at 0.5 seconds whether at the minimum or maximum range of vacuum operation. In one preferred embodiment, no rest period is provided between cycles. Accordingly, the frequency of operation of the breastpump remains at about 120 CPM, since there is no pause between cycles in the preferred embodiment. In another embodiment, a rest period of 0.0 to 0.5 seconds is provided between vacuum cycles.

Figure 10:
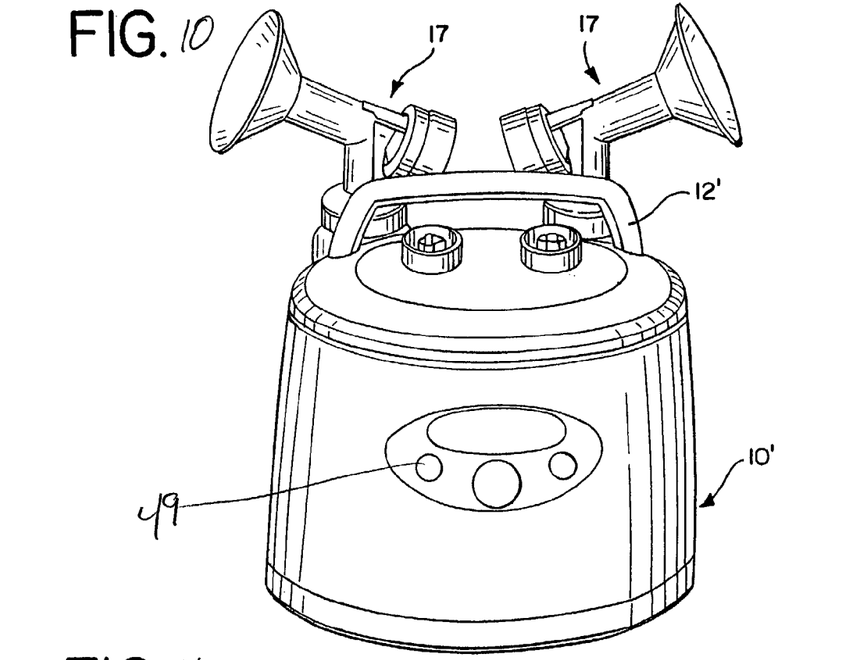
FIG. 10 is a front view of an embodiment of a motorized breastpump according to certain aspects of the present invention.
Figure 11:
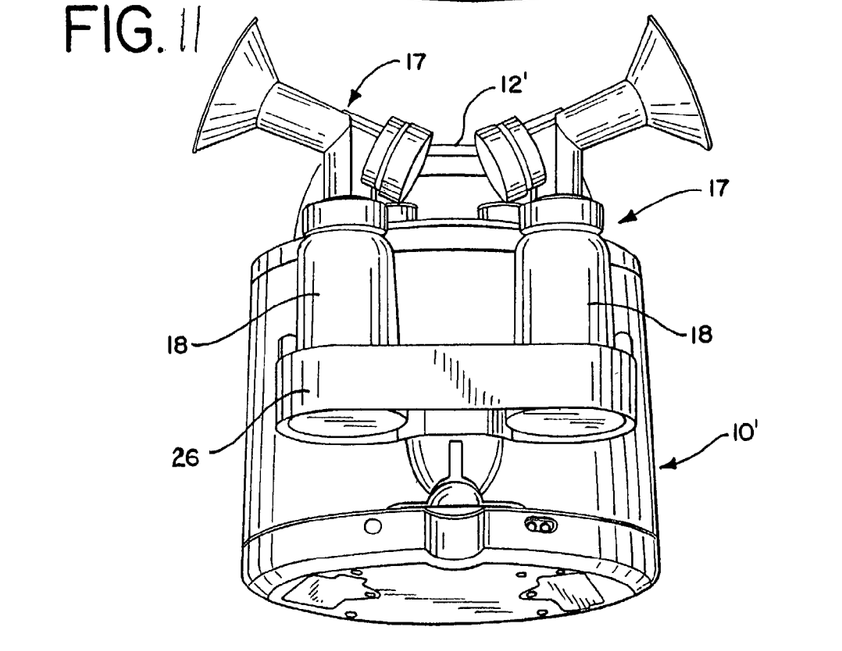
FIG. 11 is a rear view of the embodiment of FIG. 10.

FIGS. 10-13 show a motorized breastpump 10' with a handle 12'. In this embodiment the breastshields 17 are stored or carried in a holder 26 mounted to the back of the unit. FIG. 11 shows the rear of the breastpump 10' wherein the breastshields are attached to respective containers 18, which are stored in holder 26.

Figure 12:
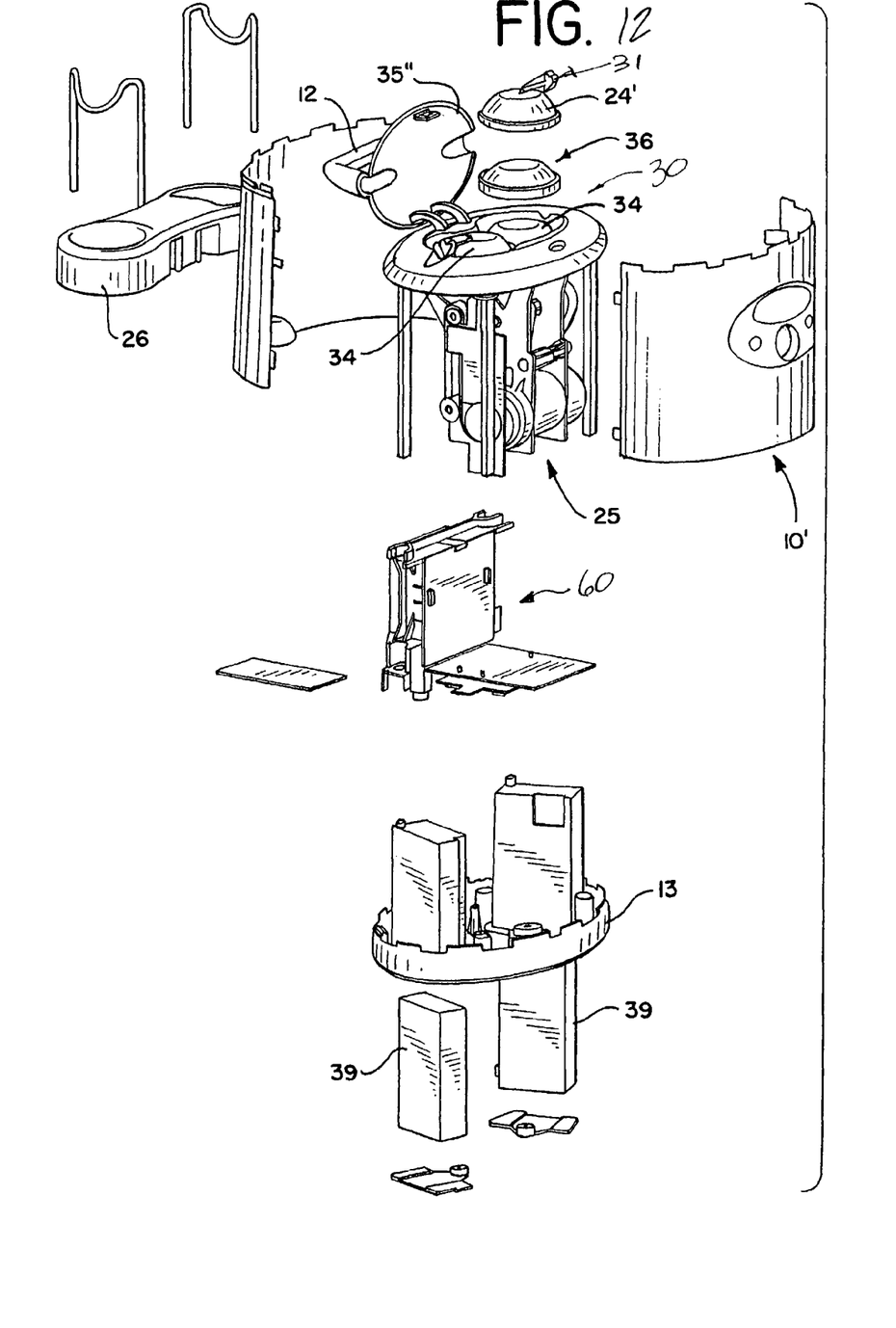
FIG. 12 is an exploded view of the embodiment of FIGS. 10 and 11.

FIG. 12 shows internal workings of the motorized breastpump of FIGS. 10 and 11. Breastpump casing 10' has a drive unit 25 mounted therein. There are, of course, any number of drives that may be used for diaphragm pumps such as those used in the instant embodiment. Indeed, the type of pump (diaphragm, piston, etc.) is not significant to certain aspects of the present invention. The driving mechanism for the breastpump shown for the embodiment in point, however, is a linear drive for the diaphragm pumps consisting of a reduction drive arrangement and a 12 V DC-motor 28.

The drive 25 may be controlled according to the arrangement shown in FIG. 4, with a power supply (e.g., batteries) 39 positioned in lower housing part 13, which provides power to drive 25 according to a microprocessor 60 positioned upon board 60'. The breastpump 10' includes a cover 35" and shells 24' for the diaphragm pump 30. The shells 24' are mounted in a removable manner in the upper housing, as through a snap fit or interference engagement, to allow easier access for cleaning or replacing the membranes 36 of the pumping mechanism, and for cleaning the shells themselves. Diaphragm members 34, may be made of any suitably durable flexible and durable fluid-impervious material (to be airtight), such as silicone with a Shore A hardness in the range of 30 to 70. The membrane and shell are in substantially airtight engagement. When the membrane 34 is pulled away from the shell, a vacuum is generated in the space between the shell interior and the membrane, which is connected via tubing connected to outlet part 31 to communicate the vacuum to a respective breastshield 17.

Prophylactic (protective) disposable/cleanable covers 36 are additionally and advantageously provided, which form-fit over the diaphragms 34 and isolate them from air and other fluid from the breastshields. The covers 36, which can be made of the same material as the membranes but thinner, are likewise fluid-impervious.

As shown in detail above, the microprocessor operates to control the drive unit 25 and, thereby pump mechanism 30, to produce pressure conditions to address different sequences of operation according to the present invention.

Again, more detail on this motor-driven embodiment can be gleaned from the priority document referenced above.

Thus, while the invention has been described herein with relation to certain embodiments and applications, those with skill in this art will recognize changes, modifications, alterations and the like which still come within the spirit of the inventive concept, and such are intended to be included within the scope of the invention as expressed in the following claims. For one example, the manually operated letdown mechanism could be a collapsible button-like device manipulated by finger pressure on a dome-shaped member to collapse the dome, which then rapidly returns to its original shape to be pressed again. The small pressure change (either positive or negative) is communicated to the nipple, and perhaps some surrounding area of the breast. Further various devices, in order to yield the letdown sequence, whether applied to a manual pump or otherwise, need not be a part of the breast shield itself or in close proximity thereto, as shown in the motorized embodiment described herein. The pressure source could further be a single source or plural sources, such as one for letdown and one for general milk expression. One source could be manually driven, while the other is motor-driven.

What is claimed is:

1. A method for breast pumping comprising:
   providing a breastshield having a portion within which a woman's breast is received for the expression of milk;
   providing a source of pressure in communication with said breastshield which is operated by a controller;
   programming said controller with a pre-set sequence to operate said source of pressure to produce at least a milk letdown sequence of rapid cycles per minute that is specifically designed to yield a milk ejection reflex (letdown) prior to milk expression and a slower milk expression sequence from said letdown sequence;
   operating said breastpump first according to said milk letdown sequence, and then
   operating said breastpump according to said milk expression sequence.

2. The method of claim 1 wherein said milk letdown sequence is provided to the user for programming said controller.

3. The method of claim 2 wherein said milk letdown sequence is provided to the user in the form of an option on the breastpump selectable by the user through a single input command.

4. The method of claim 3 wherein said input command is a switch.

5. The method of claim 2 wherein said letdown sequence is provided to the user in a form which automatically first operates said source of pressure in said letdown sequence and then substantially immediately follows with said expression sequence.

6. A method for breast pumping comprising:
   providing a breastshield having a portion within which a woman's breast is received for the expression of milk;
   providing a source of vacuum in communication with the breastshield which is operated by hand;
   providing a first mechanism manipulated by hand that is specifically dedicated and designed for manually operating said source of vacuum in a first vacuum cycle mode to produce a milk ejection reflex (letdown) sequence of rapid cycles per minute; and then
   manually operating said source of vacuum using another mechanism different from said first mechanism according to a second vacuum cycle mode, different from and slower than said first mode, for a milk expression sequence.

7. The method of claim 6 wherein said letdown sequence has a vacuum pressure ranging between about 50 mmHg to about 200 mmHg, and a frequency of about 80 to about 160 cycles per minute.

8. The method of claim 6 wherein said mechanisms are respective first and second levers.

9. The method of claim 6 wherein said levers are located on opposite ends of a handle.

10. The method of claim 9 wherein said handle has a different pivot point for each said lever.

11. A method for breast pumping comprising:
    providing a breastshield having a portion within which a woman's breast is received for the expression of milk;
    providing a source of vacuum in communication with the breastshield which is operated by hand;
    providing a first mechanism manipulated by hand that is specifically dedicated and designed for manually operating said source of vacuum in a first vacuum cycle mode to produce a milk ejection reflex (letdown) sequence of rapid cycles per minute; and then
    manually operating said source of vacuum using another mechanism different from said first mechanism according to a second vacuum cycle mode, different from and slower than said first mode, for a milk expression sequence;
    wherein said milk expression sequence is at a level of pressure greater than said letdown sequence; and
    wherein said levels of pressure are relative levels of vacuum, such that said level of vacuum for said expression sequence is a greater vacuum level than said level of vacuum for said letdown sequence.

12. A method for breast pumping comprising:

providing a breastshield having a portion within which at least part of a woman's breast is received for the expression of milk;

providing a source of pressure that is electrically-driven in communication with the breastshield;

operating said source of pressure according to a pre-set sequence constituting rapid cycles per minute in a manner that is specifically implemented so as to produce a milk ejection reflex (letdown) prior to milk expression, and then operating said source of pressure according to a slower sequence of fewer cycles per minute than said letdown sequenced in a manner that is specifically implemented so as to provide general milk expression;

wherein said milk expression sequence is at a level of pressure greater than said letdown sequence; and wherein said levels of pressure are relative levels of vacuum, such that said level of vacuum for said expression sequence is a greater vacuum level than said level of vacuum for said letdown sequence.

* * * * *